US00PP35404P2

(12) United States Plant Patent
Hansen

(10) Patent No.: US PP35,404 P2
(45) Date of Patent: Sep. 26, 2023

(54) ***ECHINACEA* PLANT NAMED 'RASPBERRY BERET'**

(50) Latin Name: ***Echinacea* hybrid**
Varietal Denomination: Raspberry Beret

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,770

(22) Filed: Nov. 16, 2022

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
See application file for complete search history.

(56) References Cited

PUBLICATIONS https://www.waltersgardens.com/variety.php?ID=ECHFB (Retrieved from the Internet on Apr. 21, 2023).*

* cited by examiner

*Primary Examiner* — Susan McCormick Ewoldt

(57) ABSTRACT

The new and distinct cultivar of *Echinacea* plant named 'Raspberry Beret' of heavily branched plants, compact habit, producing fragrant inflorescences with nearly horizontal raspberry-pink ray florets and very large disk florets of deep raspberry-pink forming a center pompon. The new plant flowers from mid-summer to late summer, and is suitable as a potted plant, for the landscape, and for cut flower arrangements.

1 Drawing Sheet

Botanical denomination: *Echinacea* hybrid.
Cultivar designation: 'Raspberry Beret'.

STATEMENT REGARDING PRIOR DISCLOSURES UNDER 37 CFR 1.77(b)(6)

The first non-enabling disclosures of the claimed plant, in the form of a photograph and brief description was on a website operated by Walters Gardens, Inc. on Dec. 1, 2021, followed by a photograph and brief description in the "Walters Gardens 2022-2023 Catalog" on Jun. 8, 2022. The claimed plant was first sold on Jul. 11, 2022, to W.W. Greenhouses, Garden Crossings, and Plant Select by Walters Gardens, Inc., who obtained the plant and all information relating thereto from the inventor. No plants of *Echinacea* 'Raspberry Beret' have been sold in this country or anywhere in the world, nor has any disclosure of the new plant been made, more than one year prior to the filing date of this application, and such sale or disclosure within one year was either derived directly or indirectly from the inventor and therefore a 35 U.S.C. § 102(b) exception.

BACKGROUND OF THE INVENTION

The present invention relates to the new and distinct cultivar of Coneflower from the genus *Echinacea* and given the cultivar name 'Raspbeny Beret'. The new plant was the result of a cross by the inventor of an unnamed proprietary hybrid known as 17-2-2 (not patented) as the female parent and an unnamed proprietary hybrid known as 17-7-x (not patented) as the male in the summer of 2018, at a wholesale perennial nursery in Zeeland, Mich. The single seedling selected was evaluated initially in trials in the summer of 2019 at the same nursery and assigned the breeder code of 18-16-2.

*Echinacea* 'Raspberry Beret' has been asexually propagated at the same nursery by crown division and also using careful shoot tip tissue culture procedures and found to reproduce plants that exhibit all the characteristics identical to the original plant in successive generations.

*Echinacea* 'Raspberry Beret' is distinct from all other Coneflowers known to the inventor. The nearest comparison cultivars are: 'Butterfly Kisses' U.S. Plant Pat. No. 24,458, 'Strawberry Mousse' (not patented), 'Razzmatazz' U.S. Plant Pat. No. 13,894, 'Little Annie' (not patented), 'Raspberry Truffle' U.S. Plant Pat. No. 22,612, and 'Secret Affair' U.S. Plant Pat. No. 24,354.

The female parent plant, 17-2-2, has a taller habit a single tow of ray florets of light pink with good basal branching. The male parent plant, 17-7-x, has a taller habit with less branching, a single row of dark pink ray florets, and large disk florets of dark pink producing a pompon effect.

'Butterfly Kisses' has a slightly taller habit and lighter pinkish-purple ray florets that droop more. and the anemone-flower-like disk florets are less yellowish-green when opening and lighter yellow with maturity. 'Strawberry Mousse' is taller in habit, inflorescences have ray florets of a lighter purplish-pink color that droop more, and the disk pompon is smaller and a lighter purplish-pink. 'Butterfly Kisses' has light pinkish-purple ray florets and a darker pompom of anemone-flower-like darker purplish-pink disk florets. 'Little Annie' has a shorter habit with single purple-pink ray florets and without anemone-flower-like disk florets. 'Raspberry Truffle' has much taller habit and the ray florets are a lighter strawberry-peach color. 'Secret Affair' has a taller habit, a single row of ray florets of a deeper pink and a large pompon disk of fewer florets of strong purplish-red that droop much more.

SUMMARY OF THE INVENTION

*Echinacea* 'Raspberry Beret' has not been evaluated under all possible environmental conditions. The phenotype may vary with variations in the environment including: growing temperature, available sunlight, nutrients, water, etc. without a change in the genotype of the plant. The new plant is distinct from its parents and'all other *Echinacea* known to the applicant in the following combined traits:

1. Fragrant inflorescences with raspberry-pink ray florets;
2. Very large disk florets of deep raspberry-pink;
3. Center pompon of disk florets that have notched apices;
4. Vigorous, compact, growth habit with heavy branching;
5. Medium-green ovate foliage.

BRIEF DESCRIPTION OF THE DRAWINGS

The photographs of 'Raspberry Beret' demonstrate the overall appearance of the plant including the unique traits. The drawings of the new plant are of a two-year-old plant grown in a full-sun trial garden in Zeeland, Mich. The colors are as accurate as reasonably possible with color reproductions. Some slight variations of color may occur as a result of lighting quality, intensity, wavelength, direction, or reflection.

DETAILED DESCRIPTION OF THE PLANT

Figure 1:
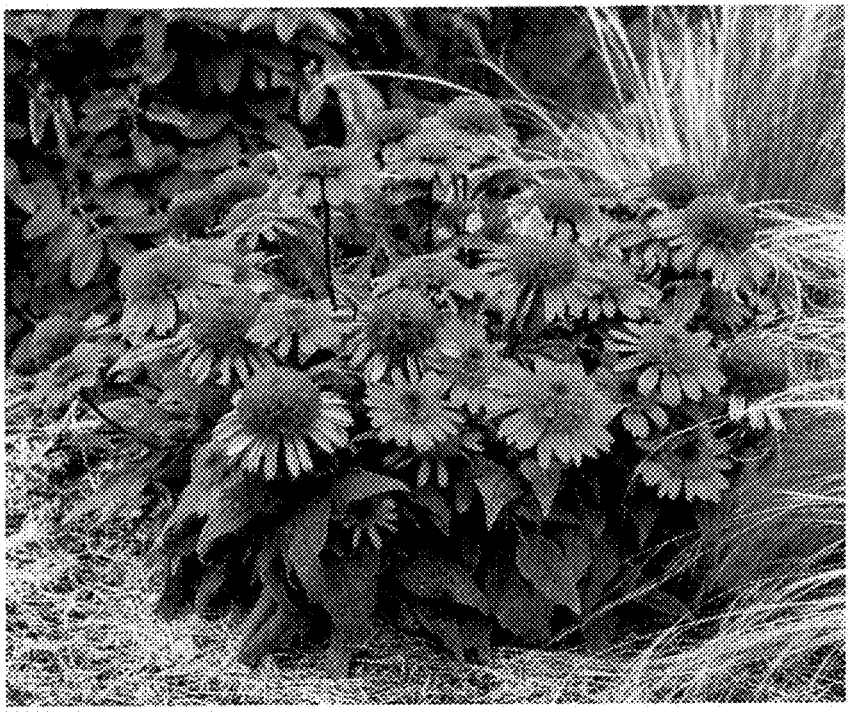
FIG. 1 shows the habit of the new plant in the flower.
Figure 2:
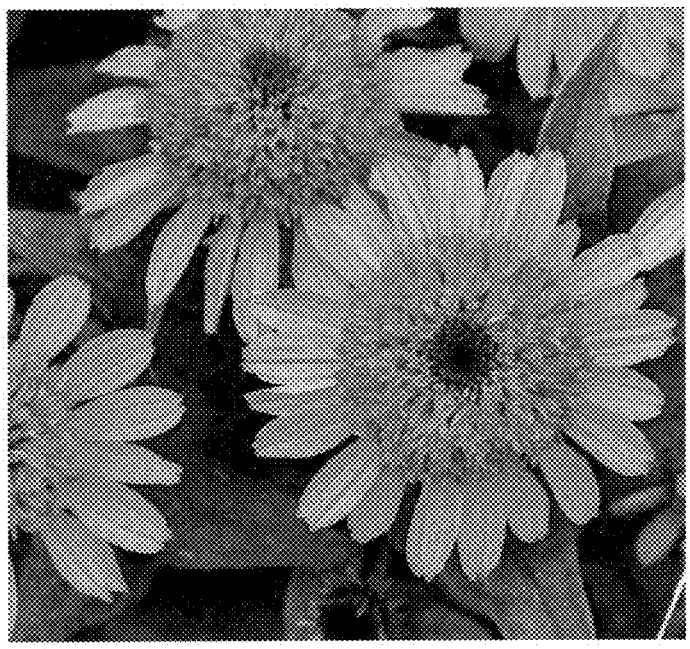
FIG. 2 shows a close-up from above of some inflorescences with flat ray florets and large center pompon.

The following description of *Echinacea* 'Raspberry Beret' is based on observations of two-year-old specimens grown in a partially-shaded greenhouse and in a full-sun trial garden in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female or seed parent is the proprietary unreleased hybrid 17-2-2 comprising a complex cross with 'Solar Flare' U.S. Plant Pat. No. 22,133, 'Little Annie' (not patented), 'Julia' U.S. Plant Pat. No. 24,629 and 'Butterfly Kisses' U.S. Plant Pat. No. 24,458 and male parent is the proprietary unreleased hybrid 17-7-x comprising a complex crossing with offspring from 'Julia', 'Solar Flare', 'Little Annie' and 'Butterfly Kisses';

Plant habit: Multi-stemmed, freely-branched, hardy herbaceous perennial, flowering to about 41 cm tall and 42 cm wide with foliage to 25 cm tall and 42 cm wide;

Growth rate: Vigorous, finishing in 4-liter containers in. about 2 months during the summer;

Roots: Cream-colored, finely-branched;

Foliage: Alternate; ovate; acute apex; cuneate base; margin micro-ciliolate and serrulate with teeth to about 2 mm long and 3 mm wide; hirsutulous abaxial and glabrous adaxial; to about 12.5 cm long and 7.3 cm wide decreasing distally, average about 8.7 cm long and 5.6 cm wide;

Leaf color: Young leaves adaxial nearest RHS 146B, abaxial nearest RHS 146A; mature leaves adaxial nearest 137B, abaxial between RHS 138A and RHS NN137D; variegation absent;

Foliage fragrance: Lightly herbal;

Venation: Pinnately three-nerved; abaxial midrib and veins costate; glabrous adaxial, hirsutulous abaxial;

Vein color: Adaxial basal midrib and basal primary veins between RHS 193A and RHS 145C, distally between RHS NN137D and RHS 138A; abaxial midrib and primary veins between RHS 145B and. RHS 146D, secondary veins between RHS 138A and RHS NN137D;

Petiole: Concavo-convex; glabrous adaxial; hirsutulous abaxial; to about 18.5 cm long and 7 mm wide at the semi-clasping base and 2.5 mm wide in middle of lowest leaves and decreasing to nearly sessile distally;

Petiole color: Adaxial center nearest 145C, margin between RHS 139A and RHS NN137A; abaxial center between RHS 146D and. RHS 145C, edge nearest RHS NN37C;

Stem: Hirsutulous; cylindrical, fistulous; strong and stiff; to about 37 cm long including peduncle and about 7 mm diameter at base; average 34 cm long and 6 mm diameter; about 3 per plant; aspect upright;

Stem color: Nearest RHS 146C;

Peduncle: Hirsutulous to pubescent; terete; strong; stiff; branched; about 10 cm long and 5 mm diameter above last leaves; quantity per stem about four to six; aspect ascending;

Peduncle color: Proximally nearest RHS 146D and nearest RHS N186C in high light exposure;

Internode: 9 to 11 per stem; average about 3.4 cm long, shorter proximally and longer distally; node color same as surrounding peduncle;

Branches: Cylindrical; hirsutulous; tightly angled to main stem to about 60° above horizontal: about 3 to 5 branches per stem; to about 22 cm long and 4.5 mm diameter;

Branch color: Proximally nearest RHS NN186C;

Inflorescence: Bracteate head, aggregate of achene; with single whorl of distinct ligulate ray florets and enlarged disk florets above pappus producing a pompon effect; flowering mid-summer to late summer, initial inflorescence largest, to about 10 cm wide and 4.5 cm tall, with inner pompon to 6.8 cm across and 3.5 cm tall; to 4 to 7 inflorescences per stem;

Inflorescence fragrance: Lightly sweet, honey-like;

Flower persistence: Remaining effective in color for 10 to 14 days depending on temperatures, cone drying on plant, and effective into winter;

Involucre: With numerous bracts, about 50 to 60 per inflorescence in 3 to 4 whorls; arcuate downward toward peduncle;

Involucre bracts: Deltoid; acute apex; truncate base; eiliolate margin; reflexed; adaxial glabrous to micro-puberulent; abaxial hirsutulous; to about 11 mm long and 4 mm across decreasing distally; color adaxial and abaxial center nearest RHS 138A, adaxial and abaxial edges between RHS 137A and RHS 137B;

Inflorescence buds with ray florets vertical and still enrolled: About 35 mm across and 25 mm tall; ray floret color nearest RHS 59B, disk florets nearest RHS 187B, and spines nearest RHS 187A;

Ray florets: Ligulate; zygomorphic; arrangement in single whorl, frequently moderately imbricate; apex emarginated with two notches, rarely four notches to 5 mm deep; base attenuate; margin entire; adaxial and abaxial surfaces matte; 16 to 23 per inflorescence; opening to horizontal, drooping up to 15 degrees below horizontal with maturity; flat, twisting absent; sterile; ray floret to 42 mm long and 18 mm wide near middle, base 2.5 mm wide; average size 39 mm long, 16 mm wide at center tapering to 2 mm wide at base; adaxial veins thickened and raised;

Ray floret color: Changing with maturity; when first horizontal young adaxial between RHS 61A, RHS 61B and RHS 64A, between RHS 59B and RHS 60B in mid-open period, and between RHS 64D and RHS 63C proximally before dropping; basal 3 to 4 mm remaining constant between RHS 146A and RHS 146D in both adaxial and abaxial; abaxial beginning between RHS 58A and RHS 59C when first horizontal, becoming nearest RHS 59C in mid-open period, and nearest RHS 186C dropping;

Disk florets: About 400 to 500 per inflorescence; zygoraorphic; perfect; produced in large raised dome about 6.8 cm across and 3.5 cm tall, individually to about 27 mm long and 7 mm wide;

*Disk floret corolla.*—Typically five tepals fused forming tube; to about 27 mm long and 7 mm wide at apex, fused in tube in basal 20 mm, free in distal 7 mm; individual disk florets about 2.5 mm wide at fusion; acute apex; entire margin; both surfaces slightly lustrous.

*Disk floret corolla tube color.*—Adaxial between RHS 53C and RHS 59C with base variable between RHS 159D to RHS 59D; abaxial between RHS 59C and RHS 59D with base nearest RHS 159D; no significant color change with maturity.

*Androecium.*—Present on disk florets only; five; synandrous.

*Staminal column.*—About 0.7 mm wide, about 4 mm long and not exserted; five fused stamens; color nearest RHS N186A.

*Anthers.*—Fused, about 2 mm long and 0.7 mm diameter; color nearest RHS N186A when present.

*Filaments.*—Five; attached to column; thin, less than 0.2 mm diameter and 2 mm long; color nearest RHS N155D.

*Pollen.*—Not observed.

*Gynoecium.*—On ray and disk florets; single; to 11.5 mm long.

*Style.*—Single main or split with up to three smaller branches; to about 7 mm long and 0.2 mm diameter with shorter split styles of various shorter lengths; color nearest RHS 170D.

*Stigma.*—Bifid; about 1 mm long and 0.1 mm diameter; color nearest RHS 182A.

*Ovary.*—Inferior; obdeltoid; to 3 mm long and 1.7 mm wide at apex; color nearest RHS 193D.

*Fruit.*—Obdeltoid; to 4 mm long and 3 mm wide at apex; color nearest RHS 199D.

Receptacle spines: With disk florets; acicular; narrowly acute apex; glabrous; lustrous; to 15 mm long and 2 mm across near middle; producing a cone about 28 mm wide and 25 mm tall;

Spine color: Adaxial and abaxial apices or distal 2 mm nearest RHS 187A, next proximal 2 mm nearest RHS 175C, middle portion nearest RHS 146C, proximal portion between RHS 145C and RHS N144A, base nearest RHS NN155B.

Disease and pest resistance: Resistance and susceptibility beyond that of other hardy Coneflower cultivars have not been observed.

Growth: The plant grows best with plenty of moisture and adequate drainage but is able to tolerate some drought when mature.

Winter hardiness: At least from USDA zone 4 through 8.

I claim:

1. A new and distinct cultivar of *Echinacea* plant named 'Raspberry Beret', as herein described and illustrated.

* * * * *